United States Patent
Tanaka et al.

(10) Patent No.: US 12,324,717 B2
(45) Date of Patent: Jun. 10, 2025

(54) DENTAL RESTORATIVE SET AND METHOD OF RESTORING TOOTH

(71) Applicant: GC Corporation, Shizuoka (JP)

(72) Inventors: Koji Tanaka, Tokyo (JP); Daizaburo Mori, Tokyo (JP)

(73) Assignee: GC Corporation, Shizuoka (JP)

( * ) Notice: Subject to any disclaimer, the term of this patent is extended or adjusted under 35 U.S.C. 154(b) by 599 days.

(21) Appl. No.: 17/593,704

(22) PCT Filed: Jan. 15, 2020

(86) PCT No.: PCT/JP2020/001015
§ 371 (c)(1),
(2) Date: Sep. 23, 2021

(87) PCT Pub. No.: WO2020/195026
PCT Pub. Date: Oct. 1, 2020

(65) Prior Publication Data
US 2022/0183788 A1    Jun. 16, 2022

(30) Foreign Application Priority Data

Mar. 27, 2019   (JP) .................................. 2019-061731

(51) Int. Cl.
*A61C 5/30*      (2017.01)
*A61C 13/15*     (2006.01)
*A61K 6/889*     (2020.01)

(52) U.S. Cl.
CPC ............ *A61C 5/30* (2017.02); *A61C 19/003* (2013.01); *A61K 6/889* (2020.01)

(58) Field of Classification Search
CPC ...................................................... A61K 6/889
See application file for complete search history.

(56) References Cited

U.S. PATENT DOCUMENTS

| | | | |
|---|---|---|---|
| 4,738,722 A | 4/1988 | Ibsen et al. | |
| 5,871,360 A * | 2/1999 | Kato ................. | A61K 6/889 |
| | | | 433/226 |
| 8,183,306 B2 | 5/2012 | Kohro et al. | |
| 2003/0083398 A1 | 5/2003 | Kawashima et al. | |
| 2010/0010115 A1 | 1/2010 | Kohro et al. | |
| 2011/0245368 A1* | 10/2011 | Yarimizu ............... | A61K 6/887 |
| | | | 523/116 |
| 2017/0290746 A1 | 10/2017 | Ida et al. | |

FOREIGN PATENT DOCUMENTS

| | | | |
|---|---|---|---|
| EP | 329268 | 1/1989 | |
| EP | 1974713 A2 * | 10/2008 | ........... A61K 6/0032 |
| JP | H01-308855 | 12/1989 | |
| JP | H01-503785 | 12/1989 | |
| JP | 2003-12430 | 1/2003 | |

(Continued)

OTHER PUBLICATIONS

Z100 Safety Data Sheet; 3M; 2015 (Year: 2015).*

(Continued)

*Primary Examiner* — Michael F Pepitone
(74) *Attorney, Agent, or Firm* — IPUSA, PLLC

(57) ABSTRACT

A dental restorative set includes a glass ionomer cement and a composite resin, wherein the composite resin contains a (meth)acrylate having an acid group.

4 Claims, 2 Drawing Sheets

(56) References Cited

FOREIGN PATENT DOCUMENTS

| | | |
|---|---|---|
| JP | 2004-051554 | 2/2004 |
| JP | 2007-091689 | 4/2007 |
| JP | 2008-189579 | 8/2008 |
| JP | 2008-189581 | 8/2008 |
| JP | 2009-40772 | 2/2009 |
| JP | 2010-018524 | 1/2010 |
| JP | 2011-126830 | 6/2011 |
| JP | 2012-171885 | 9/2012 |
| JP | 2013-193962 | 9/2013 |
| JP | 2020-515641 | 5/2020 |
| WO | 2016/042770 | 3/2016 |
| WO | 2018/187375 | 10/2018 |

OTHER PUBLICATIONS

International Search Report for PCT/JP2020/001015 mailed on Mar. 17, 2020.

Yuka Morita, "Resin Bonding to a Conventional Glass-ionomer Cement or Resin-modified Cements Conditioned with Self-etching Priming Systems" with English paritial translation, The Japanese Society of Conservative Dentistry, vol. 54 (6): 448-465, 2011, with Partial translation.

Vertise™ Flow [online] Saved on Apr. 24, 2016 [Searched on Sep. 19, 2023] Internet <https://web.archive.org/web/20160424043725/https:/www.kerrdental.com/kerr-restoratives/vertise-flow-self-adhering-flowable-composite#faqs>.

J. Sabbagh et al., "Randomized Clinical Trial of a Self•Adhering Flowable Composite for Class I Restorations: 2-Year Results" International Journal of Dentistry, vol. 2017.

Vertise Flow—Technical Bulletin] [online] [Searched on Sep. 19, 2023] Internet <https://www.kerrdental.com/resource-center/vertise-flow-technical -bulletin>.

Composites/Vertise Flow—Technical Bulletin] [online] [Searched on Sep. 19, 2023] Internet <https://www.kerrdental.com/resource-center/vertise-flow-technical -bulletin>.

Kuniko Ikeda et al., "Water Sorption and Dimensional Change of Resin-Modified Glass Ionomer Cements" Dental materials and instruments vol. 17 No. 1 41-45 (1998), with English translation.

Masao Irie, "Glass Ionomers; Its Characteristics and Clinical Applications" Department of Dental Materials, Dental School, Okayama University AD Val.6 No. 4 1988, with English translation.

Irie Masao et al., "Bonding Ability to Tooth Substrate and Flexural Properties of Resin-Modified Glass-Ionomer Luting Cement" Adhes Dent vol. 30 No. 4 2012, with English translation.

New Current Dental Dictionary, Third edition, pp. 119, 340-341, 1058, 1063, 1152, Editing representative Izumi Hara, Ishiyaku Publishing, Inc., Apr. 30, 1999, with partial English translation.

Ingrid E Andersson-Wenckert et al: "Modified Class II open sandwich restorations: evaluation of interfacial adaptation and influence of different restorative techniques", European Journal of Oral Sciences, Munksgaard International Publishers, Copenhagen, DK, vol. 110, No. 3, May 26, 2002 (May 26, 2002), pp. 270-275, XP071779831, ISSN: 0909-8836, DOI: 10.1034/J.1600-0447.2002.11210.X.

* cited by examiner

DENTAL RESTORATIVE SET AND METHOD OF RESTORING TOOTH

FIELD OF THE INVENTION

The present invention relates to a dental restorative set and a method of restoring a tooth.

BACKGROUND OF THE INVENTION

Conventionally, teeth are restored by forming a cavity, then filling and curing the cavity with a glass ionomer cement in treating caries.

However, it is desirable to improve the strength of the surface of the restorative portion has been demanded.

Accordingly, a sandwich technique for restoring teeth by combining a glass ionomer cement, bonding material, and a composite resin has been known (see, for example, Patent Document 1).

Specifically, the cavity, which is treated with a conditioner, is first filled with a glass ionomer cement, followed by curing the glass ionomer cement. Then, the cured glass ionomer cement is coated with a bonding material, followed by curing the bonding material by irradiating light. Finally, the cavity, in which the bonding material is cured, is filled with a composite resin followed by curing the composite resin.

RELATED-ART DOCUMENT

Patent Documents

Patent Document 1: Japanese Unexamined Patent Publication No. H1-503785

SUMMARY OF THE INVENTION

Problems to be Solved by the Invention

However, when bonding materials are used to restore teeth, the procedures for restoring teeth become complicated.

On the other hand, when teeth are restored without the use of bonding material, the adhesion of the cured composite resin to the cured glass ionomer cement is reduced, and marginal leakage occurs.

In one aspect of the invention, the present invention is to provide a dental restorative set and a method of restoring a tooth, which can improve the adhesion of a cured composite resin to a cured glass ionomer cement and suppress the occurrence of marginal leakage, even if the tooth is restored without using a bonding material.

Means for Solving the Problem

In one aspect of the invention, a dental restorative set includes a glass ionomer cement and a composite resin, wherein the composite resin contains a (meth)acrylate having an acid group.

In another aspect of the invention, a method of restoring a tooth includes: applying a glass ionomer cement to a predetermined area of a tooth; curing the applied glass ionomer cement; applying a composite resin to the predetermined area of the tooth; and curing the applied composite resin, wherein the composite resin contains a (meth)acrylate having an acid group.

Effects of the Invention

According to an aspect of the present invention, the present invention is to provide a dental restorative set and a method of restoring a tooth, which can improve the adhesion of a cured composite resin to a cured glass ionomer cement and suppress the occurrence of marginal leakage, even if the tooth is restored without using a bonding material.

DETAILED DESCRIPTION OF THE INVENTION

Figure 1:
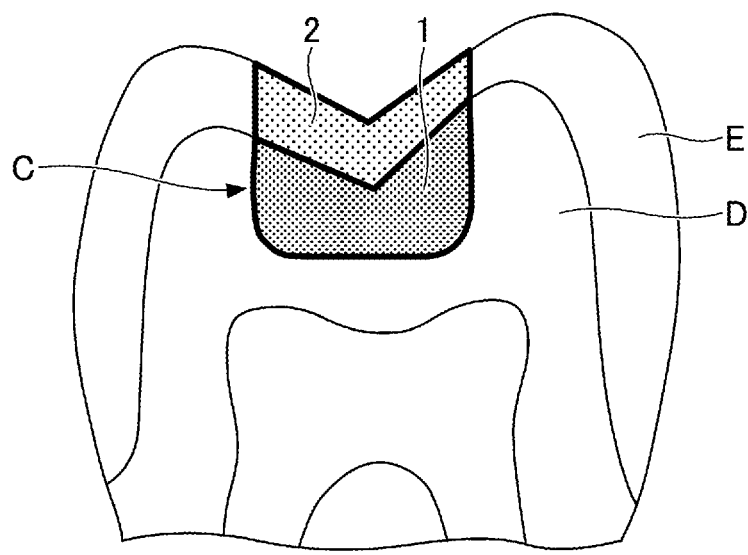
FIG. 1 is a cross-sectional schematic diagram illustrating an example of a method of restoring a tooth with a cavity formed.

Hereinafter, an embodiment for carrying out the present invention will be described. The present invention is not limited to the following embodiments, and various modifications and substitutions can be made to the following embodiments without departing from the scope of the claims.

[Dental Restorative SET]

The dental restorative set of the present embodiment includes a glass ionomer cement and a composite resin so that a restorative surface of a tooth can be composed of a cured composite resin with high strength.

The dental restorative set of the present embodiment includes a (meth)acrylate having an acid group. Therefore, the adhesion of the cured composite resin to the cured glass ionomer cement is improved and the marginal leakage is less likely to occur, even if a tooth is restored without the use of a bonding material.

Here, when a tooth is restored without using a bonding material, it is not necessary to cure the bonding material by irradiating light after the bonding material is applied. Therefore, the procedure of restoring a tooth is not complicated, and the tooth can be easily restored.

The composite resin preferably further contains a (meth)acrylate free of an acid group, a photopolymerization initiator, and a filler. This allows the composite resin to be cured by irradiating light.

The content of the filler in the composite resin is preferably 5% by mass or more and more preferably 30% by mass or more. When the content of the filler is 5% by mass or more in the composite resin, the strength of the restored surface is further improved.

It should be noted that the content of the filler in the composite resin is preferably 85% by mass or less.

The glass ionomer cement preferably contains a fluoroaluminosilicate glass powder and a liquid composition containing a polycarboxylic acid polymer, water, a (meth)acrylate, and a photopolymerization initiator. This allows the glass ionomer cement to be cured by irradiating light.

The dental restorative set of the present embodiment further preferably includes a conditioner. In this case, the application of glass ionomer cement to the region where the tooth conditioner has been applied further enhances the adhesion of the cured glass ionomer cement to the tooth.

The dental restorative set of the present embodiment may further include an etching material. In this case, the application of the etching material to a predetermined area of the tooth further enhances the adhesion of the cured composite resin to the tooth.

The dental restorative set of the present embodiment may further include a bonding material. In this case, the application of the bonding material to the predetermined area where the glass ionomer cement is cured further enhances the adhesion of the cured composite resin to the tooth and further reduces the occurrence of marginal leakage.

[Method of Restoring Teeth]

A method of restoring a tooth of the present embodiment includes a step of applying a glass ionomer cement to a predetermined area of a tooth, a step of curing the applied glass ionomer cement, a step of applying a composite resin to the predetermined area of the tooth, and a step of curing the applied composite resin. Accordingly, the restorative surface of the tooth can be composed of the cured composite resin with high strength.

In addition, the adhesion of the cured composite resin to the cured glass ionomer cement is improved and the marginal leakage is less likely to occur, even if the tooth is restored without the use of the bonding material, because the composite resin includes a (meth)acrylate having an acid group.

Here, when the tooth is restored without using the bonding material, it is not necessary to cure the bonding material by irradiating light after applying the bonding material. Therefore, the procedure of restoring a tooth is not complicated, and the tooth can be easily restored.

Areas where the glass ionomer cement is applied include, for example, in the areas of the dentin where cavities or crown defects are formed.

Areas where the composite resin is applied include, for example, the areas where the cured glass ionomer cement is formed, that is, in the areas of the enamel where cavities and crown defects are formed.

It should be noted that if the glass ionomer cement includes a fluoroaluminosilicate glass powder and a liquid composition containing a polycarboxylic acid polymer, water, a (meth)acrylate, and a photopolymerization initiator, the applied glass ionomer cement can be cured by irradiating light.

In addition, if the composite resin further includes a (meth)acrylate free of an acid group, a photopolymerization initiator, and a filler, the applied composite resin can be cured by irradiating light.

The method of restoring a tooth of the present embodiment further includes a step for applying a conditioner to a predetermined area of the tooth, and preferably applying the glass ionomer cement to the predetermined area where the conditioner for teeth has been applied. Accordingly, the adhesion of the cured glass ionomer cement to the tooth is further improved.

Areas where the conditioner is applied include, for example, in the areas of the dentin where cavities or crown defects are formed.

The method of restoring a tooth of the present embodiment further includes a step of applying an etching material to the predetermined area of the tooth, and preferably applying the composite resin to the tooth to which the etching material is applied. Accordingly, the adhesion of the cured composite resin to the tooth is further improved.

Areas where the etching material is applied include, for example, in the areas of the enamel where cavities and crown defects are formed.

The method of restoring a tooth of the present embodiment further includes a step of applying a bonding material to the predetermined area of the tooth to which the glass ionomer cement is cured, and a step of curing the applied bonding material, and a composite resin can be applied to the predetermined area to which the bonding material is applied. Accordingly, the adhesion of the cured composite resin to the tooth is further improved, and margin leakage is less likely to occur.

Areas where the bonding material is applied include, for example, in the areas of the enamel where cavities and crown defects are formed.

An example of a method of restoring a tooth with a cavity formed is illustrated with reference to FIG. 1.

First, the surface of the cavity C in the dentin D is treated with a conditioner. Then, the glass ionomer cement is filled in the area of the dentin D where the cavity C is formed, followed by curing the glass ionomer cement to form a cured glass ionomer cement 1. Next, the surface of the enamel E of the cavity C is treated with an etching material. Next, the composite resin is filled and sealed in the areas of the enamel E on the cured glass ionomer cement 1 of the cavity C, followed by curing the composite resin to form a cured composite resin 2.

The bonding material may be applied to the cured glass ionomer cement 1 before filling with composite resin, followed by curing.

Figure 2:
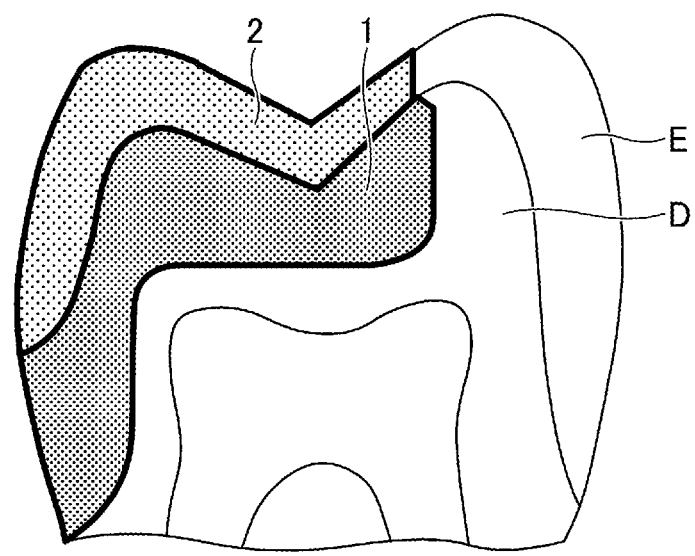
FIG. 2 is a cross-sectional schematic diagram illustrating an example of a method of restoring a tooth with a part of a crown missing.

FIG. 2 illustrates an example of a method of restoring a tooth lacking a portion of a crown (a part of dentin D and enamel E).

First, the surface of the defect in dentin D is treated with a conditioner. Then, the glass ionomer cement is applied to the area where the defect was formed in the dentin D, followed by curing to form the cured glass ionomer cement 1. Next, the surface of the defect in enamel E is treated with an etching material. The composite resin is then applied to the area in the enamel E where the defect was formed, which is the area on top of the cured glass ionomer cement 1 in the defect, followed by curing the composite resin to form a cured composite resin 2.

Here, a matrix band or the like is used in forming the cured glass ionomer cement 1 and the cured composite resin 2.

The bonding material may be applied to the cured glass ionomer cement 1 before being applied to the composite resin, followed by curing.

Figure 3:
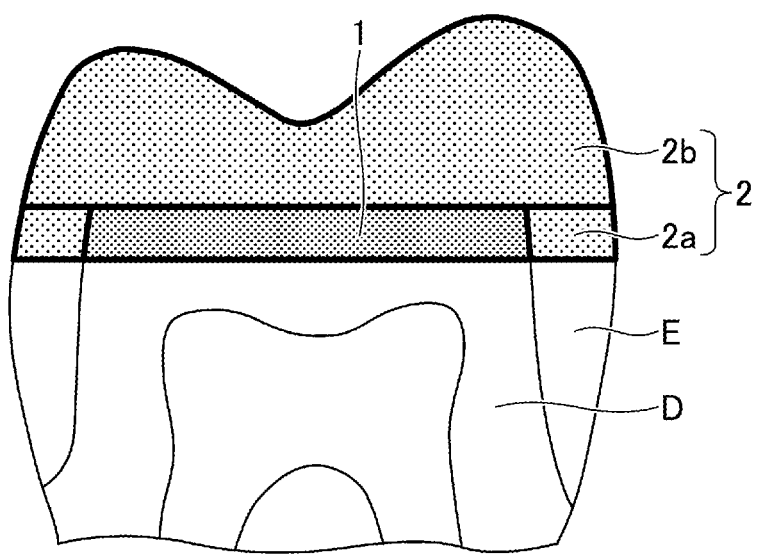
FIG. 3 is a cross-sectional schematic diagram illustrating another example of a method of restoring a tooth with a part of a crown missing.

FIG. 3 illustrates another example of a method of restoring a tooth lacking a portion of a crown (a part of dentin D and enamel E).

First, the surface of the defect in enamel E is treated with an etching material. Then, the composite resin is applied to a part of the area where the defect is formed in the enamel E, followed by curing to form the cured composite resin 2a. Next, the surface of the defect in dentin D is treated with a conditioner. Then, the glass ionomer cement is filled in a part of the area where the defect is formed in the dentin D, followed by curing to form a cured glass ionomer cement 1. Next, the composite resin is applied on the cured composite resin 2a and on the cured glass ionomer cement 1, followed by curing to form a cured composite resin 2b.

Here, a matrix band or the like is used upon forming the cured composite resin 2a and the cured composite resin 2b.

The bonding material may be applied to the cured glass ionomer cement 1 before applying the composite resin, followed by curing.

[Composite Resin]

The composite resin includes (meth)acrylate having an acid group, (meth)acrylate free of an acid group, a polymerization initiator, and a filler, but preferably, as previously described, includes a photopolymerization initiator.

((Meth)Acrylate Having an Acid Group)

As used herein and in the claims, (meth)acrylate refers to a compound (for example, monomer, oligomer, prepolymer, or the like) having one or more methacryloyloxy groups and/or acryloyloxy groups (hereinafter referred to as (meth)acryloyloxy groups).

The (meth)acrylate having an acid group preferably includes one or more phosphate, thiophosphate, or carboxyl groups.

Examples of (meth)acrylates having a phosphate group include 2-(meth)acryloyloxyethyldihydrogenphosphate, bis[2-(meth)acryloyloxyethyl]hydrogenphosphate, 2-(meth)acryloyloxyethylphenyl hydrogenphosphate, 6-(meth)acryloyloxyhexyldihydrogenphosphate, 6-(meth)acryloyloxyhexylphenyl hydrogenphosphate, 10-(meth)acryloyloxydecyldihydrogenphosphate, 1,3-di(meth)acryloylpropane-2-dihydrogenphosphate, 1,3-di(meth)acryloylpropane-2-phenylhydrogenphosphate, bis[5-{2-(meth)acryloyloxycarbonyl}heptyl] hydrogenphosphate, and the like.

Examples of (meth)acrylates having a thiophosphate group include 2-(meth)acryloyloxyethyldihydrogen thiophosphate, 3-(meth)acryloyloxypropyldihydrogen thiophosphate, 4-(meth)acryloyloxybutyldihydrogen thiophosphate, 5-(meth)acryloyloxypentyldihydrogen thiophosphate, 6-(meth)acryloyloxyhexyldihydrogen thiophosphate, 7-(meth)acryloyloxyheptyldihydrogen thiophosphate, 8-(meth)acryloyloxyoctyldihydrogen thiophosphate, 9-(meth)acryloyloxynonyldihydrogen thiophosphate, 10-(meth)acryloyloxydecyldihydrogen thiophosphate, 11-(meth)acryloyloxyundecyldihygrogen thiophosphate, 12-(meth)acryloyloxydodecyldihydrogen thiophosphate, 13-(meth)acryloyloxytridecyldihydrogen thiophosphate, 14-(meth)acryloyloxytetradecyldihydrogen thiophosphate, 15-(meth)acryloyloxypentadecyldihydrogen thiophosphate, 16-(meth)acryloyloxyhexadecyldihydrogen thiophosphate, 17-(meth)acryloyloxyheptadecyldihydrogen thiophosphate, 18-(meth)acryloyloxyoctadecyldihydrogen thiophosphate, 19-(meth)acryloyloxynonadecyldihydrogen thiophosphate, 20-(meth)acryloyloxyicosyldihydrogen thiophosphate, and the like.

Examples of (meth)acrylates having a carboxyl group include 4-(meth)acryloyloxyethyl trimellitic acid, 4-(meth)acryloyloxyethyl trimellitic anhydride, 4-(meth)acryloyloxydecyltrimellitic acid, 4-(meth)acryloyloxydecyltrimellitic anhydride, 11-(meth)acryloyloxy-1,1-undecane dicarboxylic acid, 1,4-di(meth)acryloyloxy pyromellitic acid, 2-(meth)acryloyloxyethyl maleic acid, 2-(meth)acryloyloxyethyl phthalic acid, 2-(meth)acryloyloxyethyl hexahydrophthalic acid, and the like.

Among these, 2-methacryloyloxyethyl acid phosphate and 10-methacryloyloxydecyldihydrogenphosphate are particularly preferably used in view of the adhesiveness of the composite resin to the cured glass ionomer cement.

It should be noted that two or more methacrylates having an acid group may be used in combination.

The (meth)acrylate having an acid group preferably includes two or more (meth)acryloyloxy groups. Accordingly, the strength of the restoring surface is further improved.

The content of the (meth)acrylate having an acid group in the composite resin is preferably 1 to 30% by mass, and further preferably 3 to 20% by mass. When the content of (meth)acrylate having an acid group in the composite resin is 1% by mass or more, the adhesion of the cured composite resin to the cured glass ionomer cement is further improved. When the content of (meth)acrylate having an acid group in the composite resin is 30% by mass or less, the storage stability of the composite resin is improved.

((Meth)Acrylate Free of an Acid Group)

Examples of (meth)acrylates free of an acid group include methyl (meth)acrylate, ethyl (meth)acrylate, isopropyl (meth)acrylate, n-butyl (meth)acrylate, isobutyl (meth)acrylate, hydroxypropyl (meth)acrylate, tetrahydrofurfuryl (meth)acrylate, glycidyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, 2-ethoxyethyl (meth)acrylate, 2-methylhexyl (meth)acrylate, 2-ethylhexyl (meth)acrylate, benzyl (meth)acrylate, 2-hydroxy-1,3-di(meth)acryloyloxypropane, ethylene glycol di(meth)acrylate, diethylene glycol di(meth)acrylate, triethylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylol propanetri (meth)acrylate, trimethylol ethanetri(meth)acrylate, pentaerythritol tri(meth)acrylate, trimethylol methanetri (meth)acrylate, pentaerythritol tetra(meth)acrylate, polybutylene glycol di(meth)acrylate, bisphenol A diglycidyl (meth)acrylate, di-2-(meth)acryloyloxyethyl-2,2,4-trimethylhexamethylene dicarbamate, 1,3,5-tris[1,3-bis{(meth)acryloyloxy}-2-propoxycarbonylaminohexane]-1,3,5-(1H,3H,5H)triazine-2,4,6-trione, 2,2-bis[4-(3-(meth)acryloyloxy-2-hydroxypropyl)]phenylpropane, N,N'-(2,2,4-trimethylhexamethylene)bis[2-(aminocarboxy)propane-1,3-diol]tetramethacrylate, an urethane oligomer consisting of 2,2'-bis(4-hydroxycyclohexyl)propane, 2-oxypanone, hexamethylene diisocyanate, and 2-hydroxyethyl(meth)acrylate, urethane oligomers consisting of 1,3-butanediol, hexamethylene diisocyanate, and 2-hydroxyethyl (meth)acrylate.

The (meth)acrylate free of an acid group preferably includes two or more (meth)acryloyloxy groups. Accordingly, the strength of the restoring surface is further improved.

The content of the (meth)acrylate free of an acid group in the composite resin is preferably 0.5 to 90% by mass, and further preferably 10 to 60% by mass. When the content of (meth)acrylate free of an acid group in the composite resin is 0.5% by mass or more, the adhesion of the cured composite resin to the cured glass ionomer cement is further improved. When the content of (meth)acrylate free of an acid group in the composite resin is 90% by mass or less, the storage stability of the composite resin is improved.

(Polymerization Initiator)

As the polymerization initiator, a chemical polymerization initiator and/or a photopolymerization initiator may be used.

A chemical polymerization initiator includes an oxidizing agent and a reducing agent.

Examples of the oxidizing agents in the chemical polymerization initiator include peroxides such as cumene hydroperoxide, diisopropylbenzene hydroperoxide, di-t-butylperoxide, lauroyl peroxide, benzoyl peroxide, t-butylperoxyisopropyl carbonate, t-butylperoxy-2-ethylhexanoate, and the like; azo compounds such as azobis isobutyronitrile, 1,1'-azobis (cyclohexanecarbonitrile), 2,2'- azobis (2,4-dimethylvaleronitrile), dimethyl 2,2'-azobis (2-methylpropionate), and the like; hydrogen peroxide; persulfate; and the like.

Two or more oxidizing agents may be used in combination.

The content of the oxidizing agent in the composite resin is preferably 0.001 to 10% by mass, and further preferably 0.01 to 5% by mass. When the content of the oxidizing agent in the composite resin is 0.001% by mass or more, the adhesion of the cured composite resin to the cured glass ionomer cement is further improved. When the content of the oxidizing agent in the composite resin is 10% by mass or less, the storage stability of the composite resin is improved.

As the reducing agent in the chemical polymerization initiator, amine compounds, sulfinic acids, thioureas, cysteines, ascorbic acids, or the like can be used.

Examples of amine compounds include N,N-dimethyl-p-toluidine, N,N-diethyl-p-toluidine, N,N-dimethylaniline, N,N-bis(2-hydroxyethyl)-p-toluidine, N,N-dimethylaminoethylmethacrylate, triethanolamine, methyl 4-dimethylaminobenzoate, ethyl 4-dimethylaminobenzoate, isoamyl 4-dimethylaminobenzoate, triethylamine, N-ethyldiethanolamine, triethanolamine, and the like, N-phenylglycine, and the like.

Examples of sulfinic acids include sodium p-toluenesulfinate, lithium p-toluenesulfinate, benzenesulfinic acid, sodium benzenesulfinate, p-toluenesulfonyl chloride, p-toluenesulfonyl fluoride, o-toluenesulfonyl isocyanate, sodium p-acetamidobenzenesulfinate, and the like.

Examples of thioureas include thiourea, ethylene thiourea, N-methylthiourea, N-ethylthiourea, N-propylthiourea, N-butylthiourea, N-lauryl thiourea, N-phenylthiourea, N-cyclohexylthiourea, N,N-dimethylthiourea, N,N-diethylthiourea, N,N-dipropylthiourea, N,N-di-butylthiourea, N,N-dilauryl thiourea, N,N-diphenylthiourea, N,N-dicyclohexylthiourea, trimethylthiourea, tetramethyl thiourea, N-acetylthiourea, N-benzoyl thiourea, 1-allyl-3-(2-hydroxyethyl)-2-thiourea, 1-(2-tetrahydrofuryl)-2-thiourea, and the like.

Examples of cysteines include cysteine, cysteine methyl, cysteine ethyl, N-methylcysteine, N-ethylcysteine, N-acetylcysteine, N,N-dimethylcysteine, N,N-diethylcysteine, N,N-diacetylcysteine, glutathione, and the like.

Examples of ascorbic acids include an ascorbic acid, a sodium ascorbate, a calcium ascorbate, a potassium ascorbate, and the like.

Two or more reducing agents may be used in combination.

The content of the reducing agent in the composite resin is preferably 0.001 to 10% by mass, and further preferably 0.01 to 5% by mass. When the content of the reducing agent in the composite resin is 0.001% by mass or more, the adhesion of the cured composite resin to the cured glass ionomer cement is further improved. When the content of the reducing agent in the composite resin is 10% by mass or less, the storage stability of the composite resin is improved.

Examples of the photopolymerization initiators include a ketone-based compound, an α-diketone-based compound, a ketal-based compound, an anthraquinone-based compound, a thioxanthone-based compound, a benzoin alkyl ether-based compound, an acylphosphine oxide-based compound, and the like.

Examples of ketone-based compounds include a benzophenone, a bis(4-dimethylaminophenyl)ketone, a 4,4'-bis(diethylamino)benzophenone, and the like.

Examples of α-diketone-based compounds include camphorquinone, benzyl, diacetyl, acenaphthenequinone, 9,10-phenanthrequinone, and the like.

Examples of ketal-based compounds include benzyl ketal, diacetyl ketal, benzyl dimethyl ketal, benzyl diethyl ketal, benzyl bis(β-phenylethyl)ketal, benzyl bis(2-methoxyethyl) ketal, 4,4'-dimethyl(benzyl dimethyl ketal), and the like.

Examples of anthraquinone-based compounds include anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, and the like.

Examples of thioxanthone-based compounds include thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, 2-ethylthioxanthone, 2-chlorothioxanthone, 2-hydroxy-3-(3,4-dimethyl-9-oxo-9H-thioxanthen-2-yloxy)-N,N,N-trimethyl-1-propanaminium chloride, and the like.

Examples of benzoin alkyl ether compounds include benzoin methyl ether, benzoin ethyl ether, benzoin propyl ether, benzoin isobutyl ether, and the like.

Examples of acylphosphineoxide-based compounds include 2,4,6-trimethylbenzoyl diphenyl phosphine oxide, 2,4,6-trimethoxybenzoyl diphenyl phosphine oxide, 2,6-dimethylbenzoyl diphenyl phosphine oxide, 2,6-dimethoxybenzoyl diphenyl phosphine oxide, and the like.

In addition, two or more photopolymerization initiators may be used in combination.

The content of the photopolymerization initiator in the composite resin is preferably 0.001 to 10% by mass, and further preferably 0.01 to 5% by mass. When the content of the photopolymerization initiator in the composite resin is 0.001% by mass or more, the adhesion of the cured composite resin to the cured glass ionomer cement is further improved. When the content of the photopolymerization initiator in the composite resin is 10% by mass or less, the storage stability of the composite resin is improved.

(Photopolymerization Accelerators)

When the composite resin contains a photopolymerization initiator, the composite resin may further contain a photopolymerization accelerator.

Examples of photopolymerization accelerators include tertiary amines such as N,N-dimethyl-p-toluidine, triethanolamine, tolyl diethanolamine, methyl 4-dimethylaminobenzoate, ethyl 4-dimethylaminobenzoate, isoamyl 4-dimethylaminobenzoate; barbiturate derivatives such as barbiturate, 1,3-dimethylbarbiturate, 1,3,5-trimethylbarbiturate, 1,3,5-trimethylbarbiturate, 1,3,5-triethylbarbiturate, 5-butylbarbiturate, 1-benzyl-5-phenylbarbiturate, 1-cyclohexyl-5-ethylbarbiturate, and the like.

In addition, two or more photopolymerization accelerators may be used in combination.

The content of the photopolymerization accelerator in the composite resin is preferably 0.001 to 5% by mass, and further preferably 0.01 to 1% by mass. When the content of the photopolymerization accelerator in the composite resin is 0.001% by mass or more, the adhesion of the cured composite resin to the cured glass ionomer cement is further improved. When the content of the photopolymerization accelerator in the composite resin is 5% by mass or less, the storage stability of the composite resin is improved.

(Filler)

The filler may be either an organic filler or an inorganic filler, but is preferably an inorganic filler.

Examples of inorganic fillers include silica powder, alumina powder, glass powder (for example, barium glass powder, strontium glass powder), and the like.

The inorganic filler may be treated with a surface treating agent such as a silane coupling agent and the like, as needed.

Two or more fillers may be used in combination.

(Other Components)

The composite resin may further contain a polymerization inhibitor and the like.

Examples of the polymerization inhibitors include dibutyl hydroxytoluene, 2,6-t-butyl-2,4-xylenol, and the like.

In addition, two or more polymerization inhibitors may be used in combination.

The content of the polymerization inhibitor in the composite resin is preferably 0.001 to 1% by mass and more preferably 0.01 to 0.1% by mass.

[Glass Ionomer Cement]

Glass ionomer cement includes a fluoroaluminosilicate glass powder, and includes a liquid composition containing a polycarboxylic acid-based polymer and water. As previously described, the liquid composition further preferably contains a (meth)acrylate and a photopolymerization initiator.

(Fluoroaluminosilicate Glass Powder)

The content of fluorine (F) in the fluoroaluminosilicate glass powder is preferably 1 to 35% by mass and further preferably 3 to 25% by mass.

The content of aluminum in the fluoroaluminosilicate glass powder is preferably 15 to 40% by mass and further preferably 20 to 35% by mass, in terms of the amount of aluminum oxide ($Al_2O_3$).

The content of silicon in the fluoroaluminosilicate glass powder is preferably 15 to 50% by mass and further preferably 20 to 40% by mass, in terms of the amount of silicon oxide ($SiO_2$).

The content of phosphorus in the fluoroaluminosilicate glass powder is preferably 0 to 15% by mass and further preferably 1 to 7% by mass, in terms of the amount of phosphorus(V) oxide ($P_2O_5$).

The content of calcium in the fluoroaluminosilicate glass powder is preferably 0 to 30% by mass and further preferably 1 to 20% by mass, in terms of the amount of calcium oxide (CaO).

The content of strontium in the fluoroaluminosilicate glass powder is preferably 0 to 40% by mass and further preferably 10 to 30% by mass, in terms of the amount of strontium oxide (SrO).

(Polycarboxylic Acid Polymer)

The polycarboxylic acid polymer is not particularly limited. Examples of the polycarboxylic acid polymers include a homopolymer or copolymer of α,β-unsaturated carboxylic acid.

Examples of α,β-unsaturated carboxylic acids include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, and the like.

The polycarboxylic acid-based polymer may also be a copolymer of an α,β-unsaturated carboxylic acid and a monomer capable of copolymerizing with an α,β-unsaturated carboxylic acid.

Examples of monomers capable of copolymerizing with α,β-unsaturated carboxylic acids include acrylamide, acrylonitrile, methacrylate esters, acrylates, vinyl chloride, allyl chloride, vinyl acetate, and the like.

In this case, the ratio of the α,β-unsaturated carboxylic acid to the monomer constituting the polycarboxylic acid-based polymer is preferably 50% by mass or more.

The polycarboxylic acid-based polymer is preferably a homopolymer or copolymer of acrylic acid or itaconic acid.

The polycarboxylic acid-based polymer may be at least partially powdered.

((Meth)Acrylate)

As the (meth)acrylate, a compound similar to the (meth)acrylate having an acid group or the (meth)acrylate free of acid group in the composite resin can be used.

(Photopolymerization Initiator)

As the photopolymerization initiator, a compound similar to the photopolymerization initiator in the composite resin can be used.

[Method of Applying Glass Ionomer Cement]

The glass ionomer cement is applied to a predetermined area of a tooth by kneading the liquid composition with a fluoroaluminosilicate glass powder.

The mass ratio of the fluoroaluminosilicate glass powder to the liquid composition (hereinafter referred to as the powder-liquid ratio) upon kneading the fluoroaluminosilicate glass powder and the liquid composition is preferably 1 to 6 and further preferably 1.5 to 4.5. When the powder-liquid ratio is 1 or more, the compression strength of the cured glass ionomer cement is increased. When the powder-liquid ratio is 6 or less, the liquid composition and the fluoroaluminosilicate glass powder are easily kneaded.

[Conditioner]

As a conditioner, a known conditioner can be used.

If the glass ionomer cement does not contain a (meth)acrylate or a photopolymerization initiator, a conditioner containing, for example, water and polyacrylic acid or citric acid can be used.

In addition, if the glass ionomer cement contains a (meth)acrylate and a photopolymerization initiator, a conditioner containing, for example, a (meth)acrylate having an acid group, water, ethanol, a (meth)acrylate free of acid group, and a photopolymerization initiator can be used.

As for the (meth)acrylate having an acid group, the (meth)acrylate free of acid group, and the photopolymerization initiator, compounds similar to the (meth)acrylate having an acid group, the (meth)acrylate free of acid group, and the photopolymerization initiator in the composite resin can be used.

[Etching Material]

As an etching material, a known etching material can be used.

[Bonding Material]

As a bonding material, a known bonding material may be used.

EXAMPLES

Hereinafter, examples of the present invention will be described, but the present invention is not limited to examples.

Examples 1 to 6, Comparative Examples 1 to 3

[Preparation of Glass Ionomer Cement]
(Preparation of Fluoroaluminosilicate Glass Powder)

Aluminum oxide (21% by mass), anhydrous silicic acid (44% by mass), calcium fluoride (12% by mass), calcium phosphate (14% by mass), and strontium carbonate (9% by mass) were thoroughly mixed to obtain a raw material composition. The raw material composition was then held at 1200° C. for 5 hours using a high temperature electric furnace, melted, and cooled, to prepare a fluoroaluminosilicate glass. The fluoroaluminosilicate glass was then milled using a ball mill for 10 hours and then passed through a 200 mesh (ASTM) sieve to prepare a fluoroaluminosilicate glass powder.

(Preparation of Polyacrylic Acid Solution)

The polyacrylic acid was dissolved in water to prepare 50% by mass of polyacrylic acid solution.

(Kneading)

The fluoroaluminosilicate glass powder and the polyacrylic acid solution were kneaded at a powder-liquid ratio of 1.8 to prepare a kneaded glass ionomer cement.

[Preparation of Composite Resin]

A composite resin was prepared by mixing methacrylate having a phosphate group, an inorganic filler, methacrylate free of acid group, a photopolymerization initiator, and a polymerization inhibitor as a compounding amount [part by mass] indicated in Table 1.

The meanings of the abbreviations and the preparation methods in Table 1 are as follows.

P-2M: bis(2-methacryloyloxyethyl)hydrogenphosphate
MDP: 10-methacryloyloxydecyldihydrogenphosphate
Silica powder: Aerodyl R812 (manufactured by Aerosol Japan)
Bis-MEPP: isopropylidene bis(4,1-phenylene)oxyethylene bis-methacrylate
UDMA: di-2-methacryloyloxyethyl-2,2,4-trimethylhexamethylene dicarbamate
TEGDMA: triethylene glycol dimethacrylate
CQ: camphorquinone
TPO: 2,4,6-trimethylbenzoyl diphenylphosphine oxide
EPA: ethyl 4-dimethylaminobenzoate
BHT: dibutyl hydroxytoluene (Preparation of Strontium Glass Powder)

$SiO_2$ (55% by mass), $Al_2O_3$ (10% by mass), SrO (20% by mass), and $B_2O_3$ (15% by mass) were thoroughly mixed to prepare a raw material composition. The raw material composition was then held at 1200° C. for 5 hours using a high temperature electric furnace, melted, and cooled, to prepare a strontium glass. The strontium glass was then milled for 10 hours using a ball mill and passed through a 200 mesh (ASTM) sieve to prepare a strontium glass powder.

(Preparation of Barium Glass Powder)

$SiO_2$ (55% by mass), $Al_2O_3$ (10% by mass), BaO (30% by mass), and $B_2O_3$ (10% by mass) were thoroughly mixed to prepare a raw material composition. The raw material composition was then held at 1200° C. for 5 hours using a high temperature electric furnace, melted, and cooled, to prepare a barium glass. The barium glass was then milled for 10 hours using a ball mill and passed through a 200 mesh (ASTM) sieve to prepare a barium glass powder.

(Etching Material)

ETCHANT (manufactured by GC Corporation) was used as the etching material.

(Bonding Material)

G-Premio BOND (manufactured by GC Corporation) was used as the bonding material.

(Dental Restorative Material Set)

The glass ionomer cement and the composite resin were combined with the etching material and/or the bonding material, as needed, to provide a dental restorative material set.

The dental restorative set was then used to evaluate the marginal leakage, the adhesion of the cured composite resin to the cured glass ionomer cement, and the bending strength of the cured composite resin.

[Marginal Leakage]

(Preparation of Test Pieces)

A cavity with an inner diameter of 3 mm and a depth of 2 mm was formed in a removed bovine tooth. The kneaded glass ionomer cement was then filled in the cavity formed in areas where dentin was formed (1 mm depth), followed by storing the tooth under an environment of 37° C. and 95% RH for 10 minutes to cure the glass ionomer cement. The etching material was then pretreated, as needed. Specifically, the etching material was applied to the fovea wall, allowed to stand for 30 seconds, and, after the enamel was etched, washed with water. Furthermore, the bonding material was pretreated, as needed. Specifically, the bonding material was applied to the cavity wall portion and to the cured glass ionomer cement, followed by blowing air, and irradiating the bonding material with light using a dental LED light irradiator G light prima II (manufactured by GC Corporation) to cure the bonding material. At this time, after irradiating the bonding material with light for 10 seconds, the operation of shifting the diameter of the irradiation window by half was repeated until the entire bonding material was irradiated with light. Then, the composite resin was filled in the area of the enamel where cavity was formed so as to rise slightly from the cavity, and then irradiated with light using a dental LED light irradiator G light prima II (manufactured by GC Corporation) to cure the composite resin. At this time, after irradiating the composite resin with light for 10 seconds, the operation of shifting the diameter of the irradiation window by half was repeated until the entire composite resin was irradiated with light. Then, the test pieces were stored for 24 hours at 37° C. in water, and polished while pouring water using No. 1200 water-resistant polishing paper so that the restored portion became flat to prepare the test pieces.

(Thermal Test)

A thermal test of the test pieces was performed. Specifically, the test pieces were alternately immersed for 30 seconds each in a 5° C. water bath and a 55° C. water bath for 5000 times. Then, the test pieces were immersed in 1% by mass of methylene blue aqueous solution for 4 hours, followed by removing the test pieces. Next, a precision cutting machine, ISOMET (manufactured by BUEHLER), was used to vertically cut the cavity portion, and then the degree of invasion of the methylene blue was observed to evaluate the marginal leakage. The marginal leakage was determined according to the following criteria.

Score 0: No methylene blue immersion was observed at the boundary between the cured composite resin and the tooth.

Score 1: Methylene blue immersion was observed at the boundary between the cured composite resin and the tooth.

Score 2: Methylene blue immersion was observed at the boundary between the cured glass ionomer cement and the tooth.

[Adhesion of Cured Composite Resin to Cured Glass Ionomer Cement]

(Preparation of Adhesive Samples)

A stainless steel mold with an inner diameter of 4 mm and a depth of 6 mm was filled with the kneaded glass ionomer cement, and then both ends of the mold were fixed by clamping them with stainless steel plates. The glass ionomer cement was cured at 37° C. for 1 hour. The cured glass ionomer cement was then removed from the mold and stored in water at 37° C. for 23 hours.

An acrylic resin UNIFAST II (manufactured by GC Corporation) was used to embed the cured glass ionomer cement so that the edge of the cured glass ionomer cement was exposed to prepare an adhesive sample.

(Preparation of Test Pieces)

A plastic mold with an inner diameter of 2.4 mm and a depth of 1 mm was placed on the exposed portion of the cured glass ionomer cement of the adhesive sample, followed by pretreating with the bonding material, as needed. Specifically, the bonding material was applied, followed by blowing air, and irradiating the bonding material with light using a dental LED light irradiator G light prima II (manufactured by GC Corporation) to cure the bonding material. At this time, after irradiating the bonding material with light for 10 seconds, the operation of shifting the diameter of the irradiation window by half was repeated until the entire bonding material was irradiated with light. Next, a mold was filled with the composite resin, followed by irradiating the composite resin with light using a dental LED light irradiator G light prima II (manufactured by GC Corporation) to cure the composite resin. At this time, after irradiating the composite resin with light for 10 seconds, the operation of shifting the diameter of the irradiation window by half was repeated until the entire composite resin was irradiated with light to prepare a test piece. The test piece was then removed from the mold and stored in water at 37° C.

(Shear Adhesion Test)

Twenty-four hours after preparation of the test pieces, the shear adhesion test of the test pieces was performed. Specifically, an autograph (manufactured by Shimadzu Corporation) was used to evaluate the adhesion of the cured composite resin to the cured glass ionomer cement by applying a load in the shear direction to the adhesive surface of the cured glass ionomer cement and the cured composite resin to fracture the adhesive surface. Then, the fractured surface was observed. It should be noted that the adhesion of the cured composite resin to the cured glass ionomer cement was determined based on the following criteria.

Excellent: The cured glass ionomer cement was cohesively broken.

Poor: There was fracturing at the boundary of the cured composite resin and the cured glass ionomer cement.

[Bending Strength of Cured Composite Resin]

(Preparation of Test Pieces)

A 25 mm×2 mm×2 mm stainless steel mold was filled with the composite resin, and then was pressurized by clamping with glass slides via a plastic film. The composite resin was cured by irradiating with light using a dental LED light irradiator G light prima II (manufactured by GC Corporation). At this time, after irradiating the composite resin with light for 10 seconds, the operation of shifting the diameter of the irradiation window by half was repeated until the entire composite resin was irradiated with light, and light was similarly irradiated through the two glass slides. The plastic film was then removed, and the test piece was removed from the mold. Next, burrs were removed from the test piece by using a water-resistant abrasive paper (#320), and the test piece was stored in water at 37° C.

(Bending Test)

The bending strength of the test piece was performed in accordance with ISO 4049:2009, 7.11. Specifically, the test piece was removed from water at 37° C., and the dimensions of the test piece were measured with a micrometer. Twenty-four hours after preparation of the test piece, the bending strength of the test piece was measured using an autograph (manufactured by Shimadzu Corporation) at a crosshead speed of 1 mm/min.

Table 1 indicates the evaluation results of the marginal leakage, the adhesion of the cured composite resin to the cured glass ionomer cement, and the bending strength of the cured composite resin.

TABLE 1

| | | | Examples | | | | | | Comparative Examples | | |
|---|---|---|---|---|---|---|---|---|---|---|---|
| | | | 1 | 2 | 3 | 4 | 5 | 6 | 1 | 2 | 3 |
| Pretreatment | | Etching | No | Yes | Yes | No | No | No | Yes | No | Yes |
| | | Bonding | No | No | Yes | No | No | No | Yes | No | No |
| Composite resin | Methacrylate having a phoshoric acid | P-2M | | | | 10 | | | | | |
| | | MDP | | 15 | | | 15 | 15 | | | |
| | Inorganic filler | Strontium glass powder | | 67.86 | | 66.8 | 60.8 | | | 74.77 | |
| | | Barium glass powder | | | | | | 60.8 | | | |
| | | Silica powder | | 3 | | 4 | 4 | 4 | | 2 | |
| | Methacrylate free of an acid group | Bis-MEPP | | 5 | | | | | | 4 | |
| | | UDMA | | | | 12 | 15 | 15 | | 12 | |
| | | TEGDMA | | 9 | | 7 | 5 | 5 | | 7 | |
| Photo-polymerization initiator | | CQ | | 0.03 | | 0.04 | 0.04 | 0.04 | | 0.05 | |
| | | TPO | | 0.04 | | 0.08 | 0.06 | 0.06 | | 0.07 | |
| | | EPA | | 0.06 | | 0.06 | 0.08 | 0.08 | | 0.09 | |
| Polymerization inhibitor | | BHT | | 0.01 | | 0.02 | 0.02 | 0.02 | | 0.02 | |
| Total | | | | 100 | | 100 | 100 | 100 | | 100 | |
| Marginal leakage | | | 0 | 0 | 0 | 0 | 0 | 0 | 0 | 2 | 2 |
| Adhesion of cured composite resin to cured glass ionomer cement | | | | Excellent | | Excellent | Excellent | Excellent | Excellent | Poor | |
| Bending strength of cured composite resin [MPa] | | | | 85 | | 80 | 92 | 88 | | 105 | |

From Table 1, it can be seen that using the dental restorative set of Examples 1 to 6, the adhesion of the cured composite resin to the cured glass ionomer cement is high, and marginal leakage does not occur. Here, the dental restorative sets of Examples 1, 2, 4 to 6 do not include the bonding material, and indicate high adhesion of the cured composite resin to the cured glass ionomer cement, and marginal leakage does not occur.

In contrast, the dental restorative set of Comparative Example 1 includes the composite resin that does not contain both the bonding material and the (meth)acrylate having an acid group; thus, a complicated procedure for restoring a tooth is required.

In addition, the adhesion of the cured composite resin to the cured glass ionomer cement is low, resulting in marginal leakage because the dental restorative set of Comparative Examples 2 and 3 include a composite resin that does not contain both the bonding material and the (meth)acrylate having an acid group.

This application is based on and claims priority to Japanese patent application No. 2019-061731, filed Mar. 27, 2019 with the Japan Patent Office, the entirety of which is incorporated herein by reference.

DESCRIPTION OF THE REFERENCE NUMERALS

1 Cured glass ionomer cement
2, 2a, 2b Cured composite resins
C Cavity
D Dentin
E Enamel

The invention claimed is:

1. A method of restoring a tooth comprising:
    applying a glass ionomer cement to a predetermined area of a tooth, said glass ionomer cement including water and polyacrylic acid;
    curing the applied glass ionomer cement;
    applying a composite resin to the predetermined area of the tooth where the glass ionomer cement is cured; and
    curing the applied composite resin,
    wherein the composite resin includes a (meth)acrylate having an acid group.

2. The method of restoring a tooth according to claim 1, wherein the glass ionomer cement includes a fluoroaluminosilicate glass powder, and includes a liquid composition including a polycarboxylic acid-based polymer, the water, a (meth)acrylate, and a photopolymerization initiator, and
    wherein the applied glass ionomer cement is cured by irradiating with light.

3. The method of restoring a tooth according to claim 1, wherein the composite resin further includes a (meth)acrylate free of an acid group, a photopolymerization initiator, and a filler, and
    wherein the applied composite resin is cured by irradiating with light.

4. The method of restoring a tooth according to claim 1, further comprising:
    applying an etching material to the predetermined area of the tooth; and
    applying the composite resin to the predetermined area of the tooth where the etching material is applied.

* * * * *